US006432924B1

(12) United States Patent
Nyce (10) Patent No.: US 6,432,924 B1
(45) Date of Patent: *Aug. 13, 2002

(54) METHOD OF TREATING DISORDERS CHARACTERIZED BY OVEREXPRESSION OF CYTIDINE DEAMINASE OR DEOXYCYTIDINE DEAMINASE

(75) Inventor: Jonathan W. Nyce, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/493,999

(22) Filed: Jan. 28, 2000

Related U.S. Application Data

(63) Continuation of application No. 08/772,445, filed on Dec. 26, 1993, now Pat. No. 6,136,791, which is a continuation-in-part of application No. 08/577,185, filed on Dec. 22, 1995, now abandoned.

(51) Int. Cl.[7] .............................................. A61K 31/70
(52) U.S. Cl. ............................ 514/43; 514/46; 514/49; 514/50; 514/51; 514/885; 514/908
(58) Field of Search ...................... 514/46, 49, 50, 514/51, 908, 885; 435/43

(56) References Cited

U.S. PATENT DOCUMENTS

| | | | |
|---|---|---|---|
| 3,891,623 A | 6/1975 | Vorbrüggen et al. ... | 260/211.5 R |
| 4,788,181 A | 11/1988 | Driscoll et al. | |
| 5,079,235 A | 1/1992 | Purifoy et al. ................ | 514/49 |
| 5,084,445 A | 1/1992 | Chu et al. ..................... | 514/49 |
| 5,215,971 A | 6/1993 | Datema et al. ............... | 514/49 |
| 5,576,429 A | 11/1996 | Johansson et al. ......... | 536/26.8 |
| 6,136,791 A | * 10/2000 | Nyce | |

OTHER PUBLICATIONS

T. Kulikowski et al.; Preparation and Properties of N[4]–Alkyl Analogues of 5–Methyl–2'–Deoxycytidine, Their 5'–Mono and Triphosphates, and N[4]–Alkyl Derivatives of 1,5–Dimethylcytosine, *ACTA Biochimica Polonica* 16:201–217 (1969).
J. J. Fox et al.; Thiation of Nucleosides. II. Synthesis of 5–Methyl–2'–deoxycytidine and Related Pyrimidine Nucleosides, 81:178–187 (1959).
T. Lin et al.; Synthesis and Biological Activity of Various 3+–Azido and 3'–Amino Analogues of 5–Substituted Pyrimidine Deoxyribonucleosides, *J. Med. Chem.* 26, No. 12:1691–1696 (1983).
C. K. Chu et al.; Structure–Activity Relationships of Pyrimidine Nucleosides as Antiviral Agents for Human Immunodeficiency Virus Type 1 in Peripheral Blood Mononuclear Cells, *J. Med. Chem.* 32, No. 3:612–617 (1989).
C. Kim et al.; Potential Anti–AIDS Drugs. 2',3'–Dideoxycytidine Analogues, *J. Med. Chem* 30:862–866 (1987).

F.D. Boudinot et al.; Pharmacokinetics and Metabolism of 3'Azido–2',3'–Dideoxy–5'–Methyl Cytidine in Rhesus Monkeys, *Drug Metabolism and Disposition* 21(5):855–860 (1993).
Appleboom, J. et al., "Purine Enzyme Levels in Rheumatoid Arthritis," The Journal of Rheumatology, 1985; 12:6, 1075–1077.
Thompson, P.W., et al., "Cytidine deaminase activity as a measure of acute inflammation in rheumatoid arthritis," Annals of the Rheumatic Diseases, 1986; 45, 9–14.
Stancikova, M., Rovensky, J., "Effect of Cyclosporin on the Activity of Cytidine Deaminase and Adenosine Doaminase in the Serum and Polymorphonuclear Leukocytes of Patients with Rheumatoid Arthritis," Int. J. Tiss. Reac., XV(4) 169–174 (1993).
Geborek, P., et al., "Cytidine deaminase and lactoferrin in inflammatory synovial fluids, Indicators of local polymorphonuclear cell function?" Medical Abstract: Br J Rheumatol, vol. 31, No. 4, pp. 235–240, Apr. 1992, England.
McCarthy, D.A., ET AL., "Morphological evidence that activated polymorphs circulate in the peripheral blood of patients with rheumatoid arthritis," Medical Abstract: Ann Rheum Dis, vol. 51, No. 1, Jan. 1992, pp. 13–18, England.
Helliwell, P.S., et al., "Cytidine deaminase activity, C reactive protein, histidine, and erythrocyte sedimentation rate as measures of disease activity in psoriatic arthritis," Medline Abstract: Ann Rheum Dis, vol. 50, No. 6, Jun. 1991, pp. 362–365, England.
Thompson, P.W., et al., "Evaluation of a simple method for the measurement of cytidine deaminase in serum and comparison with a reference method," Medline Abstract: Clin Chim Acta, vol. 192, No. 1, Nov. 15. 1990, pp 55–59, Netherlands.
Mansson, B., et al., "Cytidine deaminase activity in synovial fluid of patients with rheumatoid arthritis: relation to lactoferrin, acidosis, and cartilage proteoglycan release." Medline Abstract: Ann Rheum Dis, vol. 49, No. 8, Aug. 1990. pp. 594–597, England.
James. I, et al., "Determination of serum cytidine deaminase activity using ion–pair reversed–phase liquid chromatography," Medline Abstract: J Chromatogr, vol. 495, Oct. 27, 1989, pp. 105–112, England.

(List continued on next page.)

Primary Examiner—James O. Wilson
(74) *Attorney, Agent, or Firm*—Viviana Amzel, Esq.

(57) ABSTRACT

A composition, device, kit and method for countering or diagnosing cytidine deaminase or deoxycytidine deaminase over-expression or a disorder associated with it, or an increase in number or toxicity of pro-inflammatory cells that over-express cytidine deaminase or deoxycytidine deaminase or a disorder associated with it, utilizing an agent of the formula $C_7N_3H_8O_2R^1R^2XX^1$, wherein X and $X^1$ are each independently C or N, $R^1$ is lower alkyl, alkenyl and alkynyl, halogen or haloalkyl, and $R^2$ is H, $—N_3$ $—OH$, amino or halogen; or pharmaceutically acceptable salts thereof.

103 Claims, 1 Drawing Sheet

OTHER PUBLICATIONS

Jones, D.D., et al. "Serum cytidine deaminse assay—some pitfalls." Medline Abstract: Ann Rheum Dis. vol. 45, No. 1, Jan. 1986, pp. 9–14, England.

Thompson, P.W., "Evaluation of a simple method for the measurement of cytidine deaminse in serum and comparison with a reference method." Medline Abstract: Clin Chim Acta, vol. 192, No. 1, Nov. 15, 1990. pp 55–59, Netherlands.

Balzarini J, et al., "2',3'–Dideoxycytidine: Regulation of its metabolism and anti-retroviral potency by natural pyrimidine nucleoside and by inhibitors of pyrimidine nucleotitide synthesis", Molecular Pharmacology, vol. 32, No. 6, (1987), pp. 798–806.

* cited by examiner

FIGURE 1

METHOD OF TREATING DISORDERS CHARACTERIZED BY OVEREXPRESSION OF CYTIDINE DEAMINASE OR DEOXYCYTIDINE DEAMINASE

RELATED APPLICATIONS

This application is a continuation of U.S. patent application Ser. No. 08/772,445, filed Dec. 26, 1993, now U.S. Pat. No. 6,136,791; which was a continuation-in-part application of U.S. patent application Ser. No. 08/577,185, filed Dec. 22, 1995, now abandoned.

BACKGROUND OF THE INVENTION

Field of the Invention

The present invention relates to an active agent of the formula I and to treating a disorder associated in part with the overexpression of cytidine deaminase or deoxycytidine deaminase, comprising administering 5-methyl-2',3'-dideoxy-3'-azidocytidine (5mAZC), analog thereof or a pharmaceutically effective salt thereof to a subject in need of such treatment in an amount effective to treat the disorder and ameliorate its symptoms.

The overexpression of cytidine deaminase (CD) is associated with a number of human disorders. For example, certain kinds of leukemias are refractory to the widely used anti-cancer agent cytosine arabinoside (araC). The lack of response to araC has been found to be due primarily either to inactivation of the deoxycytidine kinase gene locus (whose product is required for activation of araC to its cancer-killing form), or to the overexpression of cytidine deaminase or deoxycytidine deaminase (which deactivates araC by deaminating it to an inactive form, araUracil). There is currently no adequate treatment to overcome this resistance to araC due to cytidine deaminase or deoxycytidine deaminase overexpression.

The overexpression of cytidine deaminase is also implicated in the infective cycle of the human immunodeficiency virus (HIV), the virus implicated in AIDS. The initial states of HIV infection are characterized by the overexpression of cytidine deaminase by the CD-4+T lymphocytes targeted by the virus. The elimination of this original set of infected cells could be critically important in controlling the level of subsequent infection.

Currently, one treatment for HIV infection and AIDS is the administration of 3'-azido-3'deoxythymidine associated with this treatment. Problems with toxicity, however, have been associated with this treatment. Such toxicity occurs in part due to the fact that AZT is administered systemically, and damages host cells in all replicating tissue compartments.

There is currently a need for a treatment for HIV infection that has the same or improved efficacy of AZT, without the side effects associated with toxicity. One solution to this problem would be a prodrug for AZT which exhibited reduced toxicity to replicating cells, and was preferentially activated to its virus-killing form (AZT) in HIV-infected cells.

In addition, inflammatory cells associated with the symptoms of arthritis have also been shown to overexpress cytidine deaminase.

It would therefore be desirable to provide a relatively non-toxic prodrug that is preferentially activated to a metabolite that is toxic to arthritis mediating inflammatory cells.

SUMMARY OF THE INVENTION

A method of treating a disorder associated with the overexpression of cytidine deaminase or deoxycytidine deaminase comprises administering to a subject in need of such treatment, of 5-methyl-2',3'dideoxy-3'azidocytidine (5mAZC), analog thereof or pharmaceutically acceptable salts thereof, hereinafter referred to as the "active compound", an amount effective to treat the disorder.

A method of treating a disorder associated with the overexpression of cytidine deaminase or deoxycytidine deaminase comprises administering to a subject in need of the treatment, an amount of a compound of the chemical formula I wherein X and $X_1$ are each independently C or N;

$R^1$ is lower alkyl, lower alkenyl, lower alkynyl, halogen, or haloalkyl; and $R^2$ is H, $-N_3$, $-OH$, amino, or halogen;

or a pharmaceutically acceptable salt thereof, effective to treat the disorder.

A method of combating leukemia resistant to cytosine arabinoside (araC) comprises administering to a subject in need of the treatment an anti-araC resistant leukemia effective amount of a compound of the chemical formula I.

A method of combating HIV-infection comprises administering to a subject in need of the treatment an anti-HIV effective amount of a compound of the chemical formula I.

A method of combating arthritis comprises administering an anti-arthritis effective amount of a compound of the chemical formula I to an arthritic subject.

A method of combating a cancer associated with the overexpression of cytidine deaminase, comprising administering to a subject in need of the treatment an anti-cancer effective amount of a compound of the chemical formula I.

The agent of this invention is suitable for the preparation of medicament for application in the treatments given above. The medicaments are provided in the form of oral, parenteral, topical, and transdermal formulations, as well as an implant and in the form of a kit.

DETAILED DESCRIPTION OF THE INVENTION

The method of the present invention may be used to treat a disorder associated with the overexpression of cytidine deaminase and/or deoxycytidine deaminase by administering an amount of the active compound of this invention to a subject in need of the treatment, effective to treat the disorder. That is 5-methyl 2',3'-deoxy-cytidine deaminase (5mAZC) an analog thereof, or pharmaceutically acceptable salts thereof (i.e., the active compounds). Examples of the disorders that may be treated include, but are not limited to, cancer, leukemia that is resistant to cytosine arabinoside (araC), HIV infection, and arthritis. In a preferred embodiment, the method of the present invention is used to treat a subject suffering from a cancer that is characterized by the overexpression of cytidine deaminase. Examples of these cancers include adenocarcinoma of the colon, adenocarcinoma of the lung, adenocarciona of the stomach, adenocarcinoma of the breast, Wilm's tumor, chondrocarcinoma, chondrosarcoma, leukemia, prostate tumors, brain tumors (e.g., glioma, astrocytoma), kidney tumors, pancreatic tumors, cervical tumors, liver tumors (e.g., hepatoblastoma, hepatocarcinoma), neuroblastoma, retinoblastoma, melanoma, basal cell carcinoma, sarcoma, and cancers metastatic to the liver (e.g., colon cancer).

While applicants do not wish to be bound to any particular theory of the instant invention, 5mTAZC appears to be metabolized to 3'-azido-3'deoxythymidine (AZT) by cytidine deaminase and deoxycytidine deaminase, as illustrated in Scheme 1, below.

Scheme 1

5-methyl-2', 3'-dideoxy-3'-azidocytidine
(5mAZC)

-continued

2', 3'-dideoxy-3'-azidothymidine
(also 3'-azido-3'-deoxythymidine)
(AZT)

While not adversely affecting cells that do not overexpress cytidine deaminase, 5mAZC appears to be preferentially deaminated to AZT in tumor cells that overexpress cytidine deaminase.

The present invention is concerned primarily with the treatment of human subjects but may also be employed in the treatment of other mammalian subjects, such as dogs and cats, for veterinary purposes.

As used herein, the term "lower alkyl", refers to $C^1$ to $C^4$ linear or branched alkyl, such as methyl, ethyl, propyl, butyl, isopropyl, sec-butyl, and tert-butyl. Methyl is currently preferred. As used herein the term "lower alkenyl", refers to $C^2$ to $C^5$ linear or branched alkenyl, such as ethenyl, propenyl, and butendyl. As sued herein, the term "lower alkynyl", refers to $C^2$ to $C^5$ linear or branched alykynl, such as propynyl and butynl. AS used herein, the term "haloalkyl" refers to a lower alkyl as defined above wherein one or more hydrogens is substituted with a halo-group, e.g., a chloro-, fluor-, bromo- or iodo-group, with —$CF_3$ being currently preferred.

Active compounds useful in the practice of the present invention include compounds of the chemical formula I wherein X and $X_1$ are each independently C or N;

$R^1$ is lower alkyl, lower alkenyl, lower alkynyl, halogen, or haloalkyl; and $R^2$ is H, —$N_3$, —OH, amino, or halogen.

In a preferred embodiment of the present invention, $R^1$ is methyl or —$CF_3$, and $R^2$ is —$N_3$ or —OH. In a particularly preferred embodiment of the invention, $R^1$ is methyl and $R^2$ is —$N_3$. Also encompassed herein are the pharmaceutically acceptable salts of these compounds.

Analogs of 5mAZC useful in the practice of the present invention include, but are not limited to, 5-methyl-2',3'-dideoxycytidine, 5-ethyl-2',3'-dideoxycytidine, 5-ethyl-2',3'-dideoxy-3'-azidocytidine, 5-propyl-2', 3'-dideoxycytidine, 5-propyl-2',3'-dideoxy-3'-azidocytidine, 5-propene-2', 3'dideoxycytidine, 5 propene-2', 3'-dideoxy-3'-azidocytidine, 5-propyne-2',3'-dideoxycytidine, and 5-propyne-2',3'-dideoxy-3'-azidocytidine.

The structure of 5mAZC is known. See, e.g., T. S. Lin et al., J. Med. Chem 26: 1691–1696 (1983). 5mAZC is available from ChemSyn Laboratories (Lenexa, Kans., USA). Compounds useful for carrying out the present invention may be synthesized in accordance with known procedures which will be apparent to those skilled in the art. See, e.g., T. S. Lin et al., supra; T. Kulikowski et al., Acta Biochim. Polonica 16, 201–217 (1969); J. J. Fox et al., J. Amer. Chem. Soc. 81, 178–187 (1959).

The active compounds disclosed herein may, as noted above, be prepared in the form of their pharmaceutically acceptable salts. "Pharmaceutically acceptable salts" are salts that retain the desired biological activity of the parent compound utilized and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalene sulfonic acid, methane sulfonic acid, p-toluenesulfonic acid, naphthalene-disulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The dosage of active compound for treatment will vary depending on the condition and the state of the subject being treated. Generally, the dosage may be as low as 0.1 $\mu$mol/kg, but more preferably is at least 1.0 $\mu$mol/kg and most preferably is at least 25 $\mu$mol/kg. The dosage of the active compound may generally be as high as 1000 $\mu$mol/kg, more preferably is less than 500 $\mu$mol/kg and still most preferably is less than 100 $\mu$mol/kg. Depending on the solubility of the particular formulation of active compound administered, the daily dose may be divided among one or several unit dose administrations. The administration of the active compound of the invention may be carried out therapeutically, i.e., as a rescue treatment, or prophylactically.

Pharmaceutical compositions for use in the present method of treating disorders associated with the overexpression of cytidine deaminase and/or deoxycytidine deaminase include those suitable for inhalation, oral, rectal, parenteral (including subcutaneous, intradermal, intramuscular, intravenous) and transdermal administration. The compositions may conveniently be presented in unit dosage form and may be prepared by any of the methods which are well known in the art. The most suitable route of administration in any given case may depend upon the anatomic location of the disorder in the subject, the nature and severity of the condition being treated, and the particular formulation that is being used. The formulations may conveniently be presented in unit dosage form and may be prepared by any method well known in the art.

In the present method of treating leukemia or other disorders associated with the overexpression of cytidine deaminase or deoxycytidine deaminase, the active compound is administered in a dose range as given above. The dose of active agent may vary according to the condition being treated and the dose at which adverse pharmacological effects occur. One skilled in the art will take such factors into account when determining dosage.

In one embodiment of the present invention, the active compound is administered to a subject with araC-resistant leukemia in an amount effective so that it is metabolized by cytidine deaminase or deoxycytidine deaminase to produce an anti-araC-resistant cancer effective amount of AZT.

The active compound may be used alone or in combination with one or more anti-leukemic agents for the prophylaxis or treatment of araC-resistant leukemia.

In the manufacture of a pharmaceutical composition according to the invention into a "formulation", the active agent(s) or physiologically acceptable salts thereof (the "active compound") are typically admixed with, inter alia, an acceptable carrier. The carrier must be acceptable so that it is compatible with any other ingredients in the formulation and not deleterious to the subject's health in general. The carrier may be solid or liquid, or a mixture of both, and is preferably formulated with the active compound as a unit-dose formulation, for example, a tablet, which may contain from 0.5% to 99% by weight of the active compound. One or more active compounds maybe incorporated in the formulation of the invention, e.g., the formulation may contain one or more additional agents as noted above. The formulations may be prepared by any of the well known techniques of pharmacy comprising admixing the components with one or more carriers, and optionally including one or more accessory therapeutic ingredients.

Formulations suitable for oral administration may be presented in discrete units, such as capsules, cachets, lozenges or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding in a suitable machine, the powdered compound moistened with an inert liquid binder. Liquid formulations for oral administration may optionally include enteric coatings known in the art to prevent degradation of the formulation in the stomach and provide release of the drug in the small intestine.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit/dose or multi-dose containers, for example sealed capsules and vials, and may be stored in a freeze-dried (lyophilized) condition requiring only the addition of the sterile liquid carrier, for example, saline or water-for-injection immediately prior to use. Injection solutions and suspensions maybe prepared. from sterile powders, granules and tablets of the kind previously described.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for transdermal administration may be presented as discrete patches adapted to remain in intimate contact with the epidermis of the recipient for a prolonged period of time. Formulations suitable for transdermal administration may also be delivered by iontophoresis, and typically take the form of an optionally buffered aqueous solution of the active compound. See e.g., Pharmaceutical Research 3, 318 (1986).

The following examples are provided to more fully illustrate the present invention and should not be construed as restrictive thereof. In the following examples, g means grams, h means hours, kg means kilogram, ml means milliliter, M means molar, $\mu$g means microgram, and $\mu$mol means micromoles, nmol means nanomoles, pmol means picomoles, $\mu$Ci means microCuries.

EXAMPLES

Example 1

Effect of 5mAZC in Overexpressing Cytidine Deaminase Cells

Figure 1:
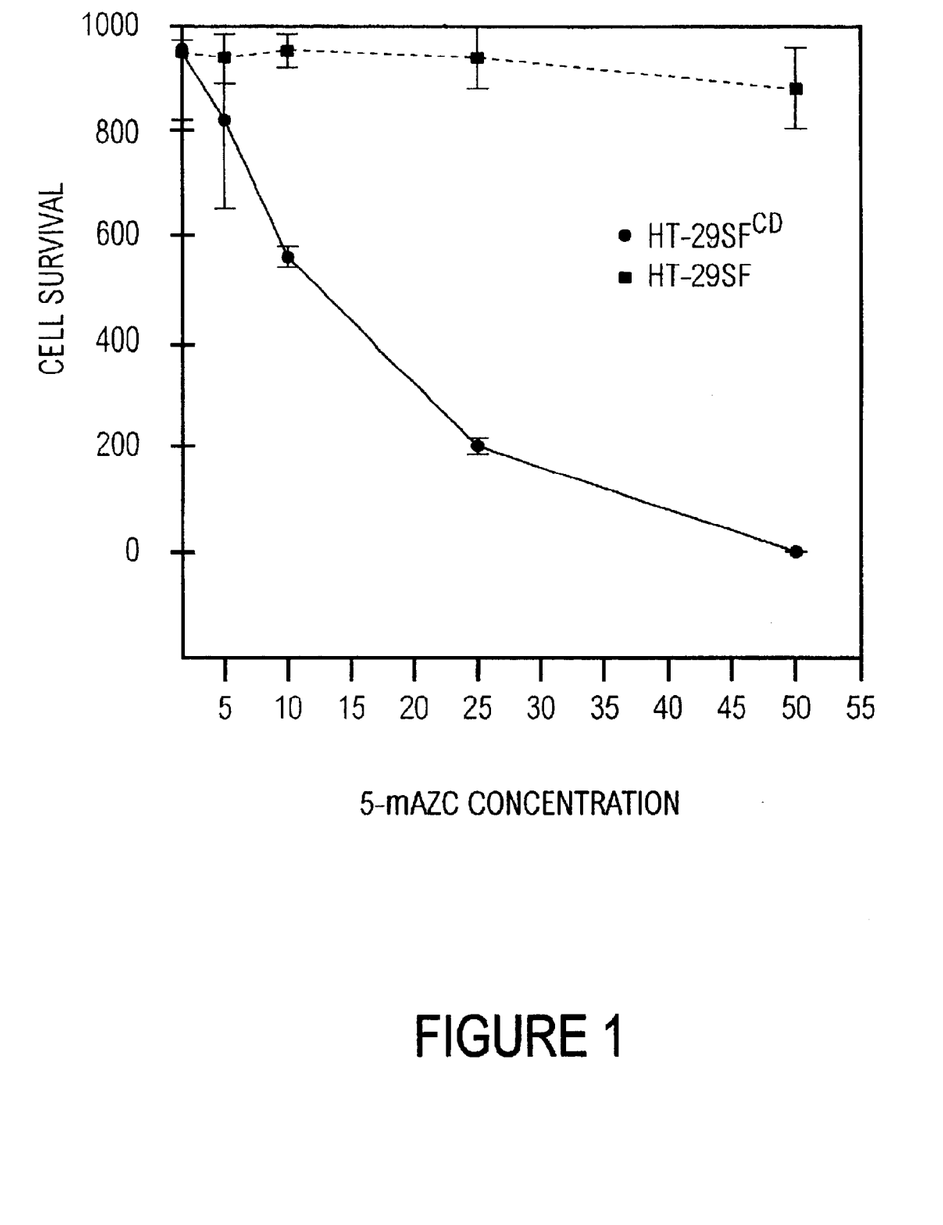
FIG. 1 is a graph of a dose response curve comparing the efficacy of 5mAZC in HT-29SF$^{CD}$ cells, which overexpress cytidine deaminase, and HT-29SF cells, which do not. HT-29SF$^{CD}$ cells are a subline of HT-29SF human colonic adenocarcinoma cells that were selected for overexpression of cytidine deaminase. HT-29SF cells were plated in the bottom compartment, and HT-29SF$^{CD}$ cells in the top compartment of a "Transwell" culture dish (1,000 cells each). A semipermeable membrane separates the two compartments of the Transwell, such that any drug administered in the tissue culture media bathe both compartments equally. 5-mAZC was administered continuously for 72 hrs. at the indicated concentrations. The numbers in the x-axis indicate the concentration (in μM) at which 5mAZC was administered continuously for 72 hours. The numbers on the y-axis indicate the number of surviving cells. The circular (●) data points represent the dose response for the HT-29SF$^{CD}$ cells. The square (■) data points represent the dose response for the HT-29SF cells.

HT-29SF human adenocarcinoma cells naturally express a high level of cytidine deaminase (CD). HT-29SF$^{CD}$ is a subline of the HT-29SF line that express even higher CD levels than normal (about 5.4 times the expression level of HT-29SF cells). In order to see whether cells that overexpress cytidine deaminase are more sensitive to 5mAZC than other cells, HT-29SF$^{CD}$ cells were plated in the top compartment of a Transwell culture dish, while HT-29SF cells were placed in the bottom compartment (1000 cells each). A semipermeable membrane separated the two compartments of the Transwell, such that drugs administered in the tissue culture media bathe both compartments equally. 5mAZC was administered continuously for 72 hrs at concentrations ranging from 0 $\mu$M to 50 $\mu$M. The results of this experiment are shown in FIG. 1. The results of this experiment confirm the idea that cells that highly overexpress CD are sensitive to 5mAZC.

Example 2

In Vitro Activity of 5mAZC

Based upon the results obtained in example 1 above, a dose of 50 $\mu$M 5mAZC was selected for more in-depth analysis. Two experiments were performed, in quintuplicate, in the same Transwell dishes, containing the HT-29SF cells and the HT-$_{29}$SF$^{CD}$ cells in compartments separated only by a membrane permeable to 5mAZC. The results are given in Table 1 below.

Table 1: Effects of exposure of HT-29SF and HF-29SF$^{CD}$ human colonic adenocarcinoma

| Experiment 1 Number of viable cells | | Example 2 Number of viable cells | |
|---|---|---|---|
| HT-29SF$^{CD}$ | HT-29SF | HT-29SF$^{CD}$ | HT-29SF |
| 33.8 ± 17.1 | 797 ± 68 | 45.4 ± 15.6 | 867.2 ± 29.4 |

Example 3

In vivo Activity of 5mAZC: Human Tumor Xenograft Model

To demonstrate that 5mAZC exhibits in vivo activity, two sixteen week old female Balb/C nu/nu mice were subcutaneously inoculated with 2.0×10$^6$HT-29SF (non cytidine deaminase producing)cells in the left scapular region, and 2.0×10$^6$HT-29SF$^{CD}$ (cytidine deaminase producing)cells in the right scapular region. One of these mice received twice daily intraperitoneal doses of 150 mg/kg of 5mAZC. The other mouse received saline only. This treatment continued for 5 weeks, at which time the animals were euthanized and the solid tumors were dissected free and weighed. The examined tumors had the following weights:

1—HT-29SF$^{CD}$+5mAZC: 0.22 g+0.31 g (N=2)

2—HT-29SF+5mAZC: 1.02±0.13 g (N=2)

3—HT-29SF$^{CD}$+saline: 0.96 g (N=1)

4—HT-29SF+saline: 1.13 g (N=1)

In another experiment, thirty BALB/c nude mice received subcutaneous injections of 5×10$^6$ HT-29SF cells. Twelve of the animals received 600 mg/kg/day 5mAZC in the flank for 28 days. Eighteen animals received saline injections on the same schedule. On Day 29, the animals were sacrificed and the tumor volume was quantified by standard methods. The average tumor volume for the control group receiving saline was 509±292 mm . In contrast, the animals treated with 5mAZC had an average tumor volume of 273±97 mm$^3$, an average 46% reduction in size. The results of Examples 2 and 3 show clearly that 5mAZC is activated in vitro and in vivo into molecular species exclusively toxic to tumor cells that overexpress cytidine deaminase.

Example 4

CD Overexpression in Colon Tumors: Ex vivo Patient Data

The hypothesis that cytidine deaminase (CD) is overexpressed in certain tumors as compared with normal tissue was demonstrated in experiments conducted with surgical specimens obtained from patient undergoing bowel resection for colon cancer. Specimens of tumor and adjacent normal tissue obtained from pathological evaluation ere assayed for CD activity using [$^3$H]-cytidine as a substrate, according to the method of R. L. Momparler and J. Laliberte, J. Leukemia Res., 14(9), 751–54 (1990). Briefly, colon tumors and adjacent mucosa from surgical specimens were homogenized in 5mM Tris-Cl, pH 7.4, sonicated on ice in three 5-second pulses, and then adjusted to 50mM Tris-HCl, pH 7.4. The homogenates were centrifuged at 12,000 ×g for 15 minutes at 4° C., and the homogenates stored at −70° C. until analysis. Protein concentration was determined using a BioRad protein assay kit and bovine gamma globulin was used as a standard.

For determination of cytidine deaminase activity, the reaction mixture (100 $\mu$L) contained 25 mM Tris-Cl, pH 7.4, 0.5 $\mu$Ci of [$^3$H]-cytidine and 0.02–0.05 mg of homogenate tissue. Reactions were carried out at 37° C. for 30 minutes, then stopped with 3 mL of cold 0.001 N HCl. The reaction mixture was placed on Whatman P-81 phosphocellulose discs that were washed with 3 mL of H$_2$O, 1 mL of 0.1 N HCl, and 3 mL of H$_2$O twice before use. The mixture was allowed to flow gently by gravity for 1 hr and then assayed for radioactivity. The results were normalized for protein content and expressed as nmol/min/mg protein. The results of this experiment are presented in Table 2 below.

TABLE 2

Ex Vivo Patient Data: Cytidine Deaminase Activity
in Tumor vs. Normal Adjacent Mucosa

| Patient | Activity in Normal Mucosa Adjacent to Tumor nmol/min/mg protein | Activity in Adeno-carcinoma Tumor n/mol/min/mg protein | Percentage Tumor CD Activity of Normal | p value |
|---|---|---|---|---|
| 1 | 13.26 ± 0.67 | 17.36 ± 0.24 | 130.92 | <.01 |
| 2 | 12.00 ± 0.50 | 15.49 ± 0.33 | 129.08 | <.01 |
| 3 | 8.81 ± 0.79 | 29.20 ± 0.54 | 331.44 | <.01 |
| 4 | 10.82 ± 0.63 | 12.98 ± 0.58 | 110/06 | <.01 |
|   |   | 18.38 ± 0.54 | 169.87 |   |
| 5 | 7.78 ± 0.22 | 9.25 ± 0.48 | 118.89 | <.05 |
| 6 | 17.32 ± 0.93 | 22.35 ± 0.39 | 129.04 | <.01 |
| 7 | 6.37 ± 0.89 | 18.69 ± 1.27 | 294.98 | <.01 |
| 8 | 9.63 ± 0.77 | 14.55 ± 1.17 | 151.09 | <.05 |
| 9 | 14.01 ± 0.89 | 20.09 ± 0.20 | 143.40 | <.01 |
| 10 | 6.06 ± 0.83 | 18.51 ± 0.89 | 305.22 | <.01 |
| Average | 10.61 ± 3.6 | 17.91 ± 5.2 | 184 |   |
| HT-29SF | 11.96 ± 0.16 |   |   |   |

Example 5

Preferential Deamination of 5mAZC to AZT in Colonic Tumors

The hypothesis that 5mAZC is preferentially deaminated to AZT in human colonic tumors versus in normal adjacent mucosa was demonstrated in the same ex vivo samples described above in Example 4. Using [$^3$H]-5mAZC as a substrate, the [$^3$H]-AZT product of the enzymatic reaction was isolated by HPLC and the radiolabeled product quantitated as described in J. W. Nyce et al., *Proc. Natl. Acad. Sci USA* 90, 2960–2964 (1993). Briefly, procedures described in Example 4 were repeated with the following exceptions: Each reaction mixture contained 0.26 µCi of [$^3$H]-5mAZC. The reactions were terminated with 50 µL of 2M perchloric acid and the mixture separated by HPLC using a 4.6×25 cm Beckman Ultrasphere ODS with a mobile phase of 12.5% acetonitrile in 40 mM sodium acetate pH 7.0. Unlabeled 5mAZC and AZT were used to authenticate the resulting peaks. The fractions corresponding to radiolabeled 5mAZC and AZT were collected and assayed for radioactivity by scintillation counting. The results were normalized for protein content and expressed as pmol/min/mg protein, and are provided below in Table 3.

To confirm that the AZT found in the colonic tumor tissue was being produced by cytidine deaminase activity (see Scheme 1, above), the cytidine deaminase inhibitor tetrahydrouridine (THU) was added to the reaction mixtures containing tumor tissue homogenate and radiolabeled 5mAZC; the amount of radiolabeled AZT produced was assayed as above, then compared to the amount of radiolabeled AZT produced in reaction mixtures not containing THU. The results of this experiment are also provided in Table 3.

TABLE 3

Ex vivo patient data: Preferential 5mAZC deamination
to AZT in tumor vs. Normal adjacent mucose

| Patient # | Radiolabeled AZT in Normal Adjacent Tissue pmol/min/mg protein | Radiolabeled AZT in Colon Tumor Tissue pmol/min/mg/protein | Percentage AZT in Tumor Tissue of Normal | p value |
|---|---|---|---|---|
| 1 | 117.14 ± 7.61 | 134.51 ± 14.92 | 114.83 |   |
|   |   | After THU: 30.56 ± 4.22 |   |   |
| 2 | 128.76 ± 2.17 | 153.34 ± 8.70 | 119.09 | <.05 |
|   |   | After THU: 50.48 ± 7.30 |   |   |
| 3 | 40.42 ± 1.18 | 304.04 ± 17.63 | 752.17 | <.01 |
|   |   | After THU: 0.31 ± 0.31 |   |   |
| 4 | 77.52 ± 8.83 | 80.01 ± 20.23 | 103.33 | polyp |
|   |   | After THU: 6.47 ± 6.47 |   |   |
|   |   | 138.58 ± 1.44 | 178.88 | <.01 |
|   |   | After THU: 34.83 ± 2.17 |   |   |
| 5 | 144.28 ± 20.39 | 225.21 ± 44.91 | 156.09 |   |
|   |   | After THU: 90.90 ± 26.41 |   |   |
| 6 | 126.75 ± 9.75 | 235.07 ± 11.74 | 185.46 | <.01 |
|   |   | After THU: 74.84 ± 6.51 |   |   |
| 7 | 70.58 ± 16.31 | 164.62 ± 20.63 | 233.23 | <.05 |
|   |   | After THU: 26.81 ± 1.46 |   |   |
| 8 | 51.91 ± 14.01 | 88.59 ± 13.80 | 170.64 |   |
|   |   | After THU: 61.31 ± 4.57 |   |   |
| 9 | 89.05 ± 13.05 | 132.10 ± 4.84 | 148.34 | <.05 |
|   |   | After THU: 39.88 ± 24.18 |   |   |

TABLE 3-continued

Ex vivo patient data: Preferential 5mAZC deamination to AZT in tumor vs. Normal adjacent mucose

| Patient # | Radiolabeled AZT in Normal Adjacent Tissue pmol/min/mg protein | Radiolabeled AZT in Colon Tumor Tissue pmol/min/mg/protein | Percentage AZT in Tumor Tissue of Normal | p value |
|---|---|---|---|---|
| 10 | 64.28 ± 6.00 | 147.80 ± 10.95 After THU: 80.34 ± 16.86 | 229.93 | <.01 |
| Average | 91.1 ± 36.0 | 172.5 ± 63 | 229 | |

The foregoing Examples are illustrative of the present invention, and are not to be construed as limiting thereof. The invention is defined by the followings claims, with equivalents of the claims to be included therein.

What is claimed as novel & unobvious in this United States Letters Patent is:

1. A pharmaceutical or veterinary composition, comprising a phamaceutically or veterinarily acceptable carrier, and an active agent that, when administered to a subject, is effective for countering or diagnosing cytidine deaminase or deoxycytidine deaminase over-expression or a disorder associated with it, or an increase in number or toxicity of pro-inflammatory cells Thai over-express cytidine deaminase or deoxycytidine dearminase or a disorder associated with it, or HIV infection or a disorder associated with HIV infection, or cancer or arthritis; the agent having the chemical formula $C_7N_3H_8O_2R^1R^2XX^1$, wherein X and $X^1$ are each independently C or N, but not simultaneously both C in the case of HIV infection or a disorder associated with HIV infection; $R^1$ is selected from lower alkyl, alkenyl and alkynyl, halogen or haloalkyl; and $R^2$ is selected from H, $-N_3$, $-OH$, amino or halogen, or pharmaceutically acceptable salts thereof.

2. The composition of claim 1, wherein in the agent $R^1$ is methyl and $R^2$ is $-N_3-$.

3. The composition of claim 1, wherein the agent is selected from the group consisting of 5-methyl-2',3'-dideoxycytidine, 5-ethyl-2',3'dideoxy-3'azidocytidine, 5-ethyl-2',3'dideoxy-3'deoxycytidine, 5-propyl-2',3'-dideoxycytidine, 5-propyl-2',3'-dideoxy-3'-azidocytidine, 5-propene-2',3'-dideoxy-3'azidocytidine, 5-propene-2', 3'dideoxycytidine, 5-propyne-2',3'-dideoxycytidine and 5-propyne-2',3'dideoxy-3'azidocytidine.

4. The composition of claim 1, having the structural formula or pharmaceutically acceptable salts thereof.

5. The composition of claim 4, wherein in the agent X comprises N and $X^1$ comprises C.

6. The composition of claim 4, wherein in the agent X comprises C and $X^1$ comprises N.

7. The composition of claim 4, wherein in the agent X comprises N and $X^1$ comprise N.

8. The composition of claim 4, wherein in the agent X and $X^1$ comprise N.

9. The composition of claim 1, wherein in the agent further comprises a radiolabel.

10. The composition of claim 1, which is freeze-dried or lyophilized.

11. The composition of claim 1, wherein in the agent the $R^1$ comprises haloalkyl selected from alkyl substituted by one or more chloro, fluoro, bromo or iodo.

12. The composition of claim 10, wherein in the agent the $R^1$ fluoroalkyl comprises $-CF_3$.

13. The composition of claim 1, comprising about 0.5 to about 99% of the agent.

14. The composition of claim 1, in unit or multi-dosage form.

15. The composition of claim 1, in liquid or solid form.

16. The composition of claim 1, in a form selected from capsules, cachets, pastilles, lozenges, powder, granules, solution, suspension, emulsion or tablets.

17. The composition of claim 1, wherein the carrier comprises a gaseous, solid or liquid carrier.

18. The composition of claim 1, further comprising an agent selected from other therapeutic agents, flavoring, suspending, thickening or surface active agents, lubricants, binders, diluents, dispersants, antioxidants, buffers, bacteriostars or solutes to attain blood isotonicity.

19. The composition of claim 18, wherein the therapeutic agent comprises an anti-leukemia or anti-arthritis agent.

20. The composition of claim 18, wherein the flavoring and inert diluent are selected from the group consisting of sucrose, acacia, tragacanth, gelatin and glycerin.

21. The composition of claim 1, in the form of an inhalable, oral, parenteral, rectal, buccal, sub-lingual, transdermal of iontophoretic formulation.

22. An inhalable formulation, comprising the composition of claim 21, and a carrier suitable for administration by inhalation.

23. The inhalable formulation of claim 22, which comprises a solid powder formulation.

24. The inhalable formulation of claim 22, which is in the form of a liquid solution, suspension of emulsion.

25. An inhalation device, comprising the formulation of claim 22.

26. An inhalation kit, comprising, in separate containers, an inhalation device, the agent of claim 22, and instruction for preparing an inhalation formulation and for its use.

27. The inhalation kit of claim 26, wherein the active agent in provided if the form of an inhalable formulation further comprising a carrier suitable for administration by inhalation.

28. An oral formulation comprising the composition of claim 21, and a carrier suitable for oral administration.

29. The oral formulation of claim 28, provided with an eteric coating.

30. A sub-lingual formulation comprising the composition of claim 21, and a carrier suitable for sub-lingual administration.

31. The sub-lingual formulation of claim 30, further comprising a flavoring agent and inert diluent selected from sucrose, acacia, tragacanth, gelatin of glycerin.

32. A parental formulation, comprising the composition of claim 21, and a carrier suitable for parenteral administration.

33. The parenteral formulation of claim 32, comprising a solution, suspension or emulsion of the active agent.

34. The composition of claim 20, in unit form provided if vials.

35. A buccal formulation, comprising the composition of claim 21, and a carrier suitable for buccal administration.

36. A rectal formulation comprising the composition of claim 21, and a carrier suitable for rectal administration.

37. The rectal formulation of claim 36, in the form of a suppository.

38. A transdermal formulation comprising the composition of claim 21, and a carrier suitable or transdermal administration.

39. A patch for transdermal delivery, comprising the formulation of claim 38.

40. A transdermal delivery kit, comprising a delivery device, and in a sealed container the formulation of claim 38, and instructions for its administration.

41. An iontophoretic formulation, comprising the composition of claim 21, and a medium suitable for iontophoretic delivery.

42. An iontophoretic delivery device, comprising a transdermal delivery device, the formulation of claim 41, and means for iontophoretic delivery.

43. An iontophoretic delivery fit, comprising the iontophoretic delivery device, and in sealed container the formulation of claim 41, and instructions for loading the formulation into the device and for use of the device.

44. A diagnostic or therapeutic kit, comprising
a delivery device;
in a separate container, the agent of claim 1, and
instructions for the preparation of a formulation effective for countering or diagnosing cytidine deaminase or deoxycytidine deaminase over-expression or a disorder associated with it, or an increase in number or toxicity of pro-inflammatory cells that over-express cytidine deaminase or deoxycytidine deaminase or a disorder associated with it, or HIV infection, or cancer, or arthritis, and for its administration.

45. The kit of claim 44, wherein the agent is provided as a composition further comprising a pharmaceutically or veterinarily acceptable carrier.

46. A method for diagnosing cytidine deaminase or deoxycytidine deaminase over-expression or a disorder associate with it, or an increase in number or toxicity of pro-inflammatory cells that over-express cytidine deaminase or deoxycytidine deaminase or a disorder associated with it, of HIV infection or a disorder associated with HIV infection, or cancer, or arthritis, comprising
(a) contacting under effective conditions an amount of an active agent with cells or tissue from a suspect site of a subject suspected of being afflicted with cytidine deaminase or deoxycytidine deaminase over-expression or a disorder associated with it, or an increase in number or toxicity of pro-inflammatory cells that over-express cytidine deaminase or deoxycytidine deaminase or a disorder associated with it, or HIV infection or a disorder associated with HIV infection, or cancer, or arthritis, the agent having the chemical formula $C_7N_3H_8O_2R^1R^2XX^1$, wherein X and $X^1$ are each independently C or N; $R^1$ selected from lower alkyl, alkenyl and alkynyl, halogen or haloalkyl; $R^2$ is selected from H, $—N_3$, $—OH$, amino or halogen, or pharmaceutically acceptable salts thereof;

(b) determining the relative toxicity of the active agent on the suspect cells or tissue versus a control conducted without the active agent; and (c) concluding that the subject is afflicted with cytidine deaminase or deoxycytidine deaminase over-expression or with a disorder associated with it, or an increase in number or toxicity of pro-inflammatory cells that over-express cytidine deaminase or deoxycytidine deaminase or a disorder associated with it, or with HIV infection or with a disorder associated with HIV infection, or with cancer or with arthritis, if the active agent has a toxic effect on the suspect cell or tissue significantly greater than that on the cells or tissue.

47. The method of claim 46, further comprising
repeating steps (a) and (b) with cells or tissue obtained from a normal site related to the subject site and a control for the normal cells conducted in the absence of the active agent; and
assessing the relative degree of toxicity of the active agent on the suspect cells or tissue versus that on the normal cells; and
conducting step (c) by comparing the relative toxicity of the active agent on the suspect versus the normal cells, and concluding that the subject is afflicted with cytidine deaminase or deoxycytidine deaminase over-expression or a disorder associated with it, or an increase in number or toxicity of pro-inflammatory cells that over-express cytidine deaminase or deoxycytidine deaminase or a disorder associated with it, or HIV infection or a disorder associated with HIV infection, or cancer, or arthritis, if the toxicity of the active agent on the suspect cell is statistically significantly greater than on normal cells or tissue.

48. The method of claim 46, wherein the active agent and the cells or tissue are contacted in vitro, ex vivo or in vivo.

49. The method of claim 46, wherein the agent further comprises an operatively linked label, which is employed to determine whether the active agent is toxic to the cells or tissue.

50. The method of claim 49, wherein the label comprises a radiolabel.

51. The method of claim 46, being applied to follow the effect of a therapy course.

52. The method of claim 46, wherein the subject is a human or a non-human animal.

53. The method of claim 46, wherein the cells or tissue comprise pro-inflammatory cells or tissue.

54. The method of claim 46, wherein the cells or tissue comprise lymphocytes.

55. The method of claim 54, wherein the cells or tissue comprise T-lymphocytes.

56. The method of claim 46, wherein the cells or tissue comprise infected with HIV virus.

57. The method of claim 46, wherein the cells or tissue comprise cancer cells or tissue.

58. The method of claim 47, wherein the normal cells or tissue comprise cells or tissue adjacent to the suspect cells or tissue.

59. The method of claim 46, wherein the diagnosed disorder is associated with HIV infection.

60. The method of claim 59, wherein the diagnosed disorder comprises HIV infection.

61. The method of claim 46, wherein the diagnosed disorder comprises arthritis, and the cells or tissue comprise(s) pro-inflammatory cells or tissue.

62. The method of claim 46, wherein the diagnosed disorder comprises cancer.

63. The method of claim 62, wherein the diagnosed cancer is selected from adenocarcinomas, sarcomas, cytomas, melanomas, or Wilm's, leukemia, brain, prostate, kidney, pancreatic, colon, liver or cervical tumors.

64. The method of claim 62, wherein the diagnosed tumors comprise brain tumors that are selected from gliomas or blastomas.

65. The method of claim 63, wherein the diagnosed tumors comprise adenocarcinomas that are selected from chondrocarcinomas, hepatocarcinomas, basal cell carcinomas or colon, lung, stomach or breast adenocarcinomas.

66. The method of claim 62, wherein the diagnosed cancer is selected from chondrosarcomas, gliomas, astrocytomas, melanomas or sarcomas.

67. The method of claim 63, wherein the diagnosed tumors comprise blastomas that are selected from hepatoblastomas, neuroblastomas or retinoblastomas.

68. The method of claim 48, which is an in vivo method, wherein the active agent is administered to the subject by inhalation, parenterally, orally, buccaly, sub-lingually, rectally, transdermally, or iontophoretically.

69. The in vivo diagnostic method of claim 48 wherein the active agent is administered in an amount of about 0.1 to about 1000 µmol/kg body weight of the subject.

70. The diagnostic method of claim 46, wherein the diagnosed disorder is associated with an increase in number or toxicity of pro-inflammatory cells that over-express cytidine deaminase or deoxycytidine deaminase.

71. The diagnostic method of claim 46, wherein the diagnosed disorder is associated with HIV infection.

72. The method of claim 62, wherein the diagnosed cancer comprises cytosine arabinoside (araC)-resistant leukemia.

73. The method of claim 46, wherein upon a positive diagnosis, the method further comprises administering to the subject an anti-diagnosed disorder effective amount of the active agent.

74. The method of claim 48, wherein when in vivo the active agent is administered systematically or dermally.

75. The method of claim 74, wherein the active agent is administered by inhalation, or orally, rectally, bucally, sub-lingually, parenterally, transdermally, or iontophoretically.

76. The method of claim 75, wherein the active agent being administered parenterally are administered subcutaneously, intradermally, intramuscularly, or intraveneously.

77. The method of claim 73, wherein the active agent is administered in an amount of about 0.1 to about 1000 µmol/kg body weight.

78. A method for treating cytidine deaminase or deoxycytidine deaminase over-expression or a disorder associated with it, or an increase in number or toxicity of pro-inflammatory cells that over-express cytidine deaminase or deoxycytidine deaminase or a disorder associated with it, or HIV infection or a disorder associated with HIV infection, or cancer, or arthritis, comprising administering to a subject in need of treatment a composition comprising a therapeutic amount of the active agent of claim 1.

79. The method of claim 78, wherein the composition comprises a radiolabel.

80. The method of claim 78, wherein the agent further comprises an operatively linked label.

81. The method of claim 80, wherein the label comprises a radiolabel.

82. The method of claim 78, wherein the subject is human or non-human animal.

83. The method of claim 78, wherein the disorder comprises arthritis, and the active agent is administered in an anti-arthritic effective amount.

84. The method of claim 78, wherein the disorder is associated with HIV infection.

85. The method of claim 84, wherein the disorder comprises HIV infection, and the active agent is administered in an anti-HIV infection effective amount.

86. The method of claim 78, wherein the disorder is associated with an increase in number or toxicity of pro-inflammatory cells that over-express cytidine deaminase or deoxycytidine deaminase, and the active agent is administered in an anti-inflammatory effective amount.

87. The method of claim 78, wherein the disorder comprises cancer, and the active agent is administered in an anti-cancer effective amount.

88. The method of claim 87, wherein the cancer is selected from adenocarcinomas, sarcomas, cytomas, melanomas, or Wilm's, leukemia, brain, prostate, kidney, pancreatic, colon, liver or cervical tumors.

89. The method of claim 88, wherein the tumors comprises brain tumors that are selected from gliomas or blastomas.

90. The method of claim 88, wherein the tumors comprise adenocarcinomas that are selected from chondrocarcinomas, hepatocarcinomas, basal cell carcinomas or colon, lung, stomach or breast adenocarcinomas.

91. The method of claim 87, wherein the cancer is selected from chondrosarcomas, gliomas, astrocytomas, melanomas or sarcomas.

92. The method of claim 88, wherein the tumors comprise blastomas that are selected from hepatoblastomas, neuroblastomas or retinoblastomas.

93. The method of claim 87, wherein the cancer comprise cytosine arabinoside (araC)-resistant leukemia.

94. The method of claim 78, wherein the cells or tissue comprise(s) pro-inflammatory cells or tissue.

95. The method of claim 78, wherein the cells or tissue comprise lymphocytes.

96. The method of claim 95, wherein the cells or tissue comprise(s) T-lymphocytes.

97. The method of claim 78, wherein the cells or tissue comprise(s) HIV infected cells or tissue.

98. The method of claim 78, wherein the cells or tissue comprise(s) cancer cells or tissue.

99. The method of claim 96, wherein the cells tissue comprise(s) cytosine arabinoside (araC)-resistant leukemia cells or tissue.

100. The method of claim 78, wherein the active agent is administered in an amount of about 0.1 to about 1000 µmol/kg body weight of the subject.

101. The method of claim 78, wherein the active agent is administered systematically or dermally.

102. The method of claim 101, wherein the active agent is administered to the subject by inhalation, or parenterally, orally, bucaly, sub-lingually, rectally, transdermally or iontophoretically.

103. The method of claim 102, wherein the active agent is administered subcutaneously, intradermally, intramuscularly or intraveneously.

* * * * *